(12) United States Patent
Toda (10) Patent No.: US 6,239,447 B1
(45) Date of Patent: May 29, 2001

(54) RADIATION IMAGE READING APPARATUS (75) Inventor: Haruyuki Toda, Hino (JP)

(73) Assignee: Konica Corporation, Tokyo (JP)

( * ) Notice: Subject to any disclaimer, the term of this patent is extended or adjusted under 35 U.S.C. 154(b) by 0 days.

(21) Appl. No.: 09/266,309

(22) Filed: Mar. 1, 1999

(30) Foreign Application Priority Data

Mar. 17, 1998 (JP) .................................................. 10-085112
Apr. 2, 1998 (JP) .................................................. 10-089631
Apr. 2, 1998 (JP) .................................................. 10-089632

(51) Int. Cl.$^7$ .................................................. G03B 42/02
(52) U.S. Cl. .................................................. 250/584; 250/581
(58) Field of Search .................................................. 250/584, 581, 250/580, 369

(56) References Cited

U.S. PATENT DOCUMENTS

| | | | |
|---|---|---|---|
| 4,739,480 | * 4/1988 | Oono et al. | 250/584 |
| 5,001,569 | * 3/1991 | Shigyo | 358/296 |
| 5,335,172 | * 8/1994 | Matsumato et al. | 250/582 |
| 5,493,128 | * 2/1996 | Boutet | 250/584 |
| 5,592,374 | * 1/1997 | Fellegara et al. | 705/3 |
| 5,757,021 | * 5/1998 | Dewaele | 250/581 |
| 5,917,536 | * 6/1999 | Kunimoto | 347/247 |

* cited by examiner

Primary Examiner—Constantine Hannaher
Assistant Examiner—Albert Gagliardi
(74) Attorney, Agent, or Firm—Frishauf, Holtz, Goodman, Langer & Chick, P.C.

(57) ABSTRACT

There is described a radiation image reading apparatus, which includes a memory to memorize information regarding each of a plurality of subjects as reservation data for each subject, a plurality of slots into each of which a recording medium recording a radiation image can be loaded, a selector to select at least one reservation data for a subject from the plural reservation data, a correlating unit to correlate the selected reservation data with at least one of the plurality of slots, a registration list preparing unit to preparing a registration list based on the selected reservation data and a display to display the registration list.

19 Claims, 12 Drawing Sheets

| SLOT1 | SLOT2 | SLOT3 | SLOT4 | SLOT5 |
|---|---|---|---|---|
| WAITING | COMPLETION | READY | WAITING | WAITING |
| 761 | 762 | 763 | 764 | 765 |

FIG. 12 (b)

| SLOT1 | SLOT2 | SLOT3 | SLOT4 | SLOT5 |
|---|---|---|---|---|
| WAITING | COMPLETION | READING | WAITING | WAITING |
| 761 | 762 | 763 | 764 | 765 |

RADIATION IMAGE READING APPARATUS

BACKGROUND OF THE INVENTION

The present invention relates to an image reading apparatus which registers an image recorded on an recording medium to be read by the apparatus, and displays the registration list on a display.

When a radiation ray, such as an X-ray, an α-ray, a β-ray, a γ-ray, an ultraviolet-ray, etc., is irradiated on a certain type of phosphor material, the radiation energy is stored in the phosphor material. Then, by irradiating an excitation light on it, a stimulative luminescence is generated in accordance with the radiation energy stored in the phosphor material. The phosphor material having the abovementioned property is known as a storage phosphor material or a photo-stimulable phosphor material.

Photo-stimulable phosphor material can be utilized for temporarily recording radiation image information of a human body, etc. on a sheet-shaped storage phosphor material (called a radiation image converting plate, or a photo-stimulable phosphor plate). The radiation image converting plate can be scanned by an excitation light, such as a laser beam, etc., to generate image signals by electronically reading the generated stimulative luminescence.

A conventional reading apparatus designates a specific image by reading a bar-code label stuck on a cassette, which corresponds to its reservation for image reading. In this method, however, there have been problems, such as a registration list of them is not displayed and the reading operation can only be performed one by one. In addition, it is troublesome to stick a bar-code label on each cassette and additionally to provide a bar-code reader. Further, it is a time-consuming task to manually operate the bar-code reader for reading each of the bar-codes.

SUMMARY OF THE INVENTION

As a solution of the cited shortcomings, it is an objective of the present invention to provide an image reading apparatus with good maneuverability.

To overcome the cited shortcomings, the objective of the present invention can be attained by a radiation image reading apparatus comprising:

a memory to memorize information regarding each of a plurality of subjects as reservation data for each subject;

a plurality of slots into each of which a recording medium recording a radiation image can be loaded;

selecting means for selecting at least one reservation data for a subject from the plural reservation data;

correlating means for correlating the selected reservation data with at least one of the plurality of slots;

registration list preparing means for preparing a registration list based on the selected reservation data; and a display to display the registration list.

Further, in order to overcome the cited shortcomings, the present invention also embodies the following:

(1) The image reading apparatus, embodied in the present invention, comprises a plurality of slots for inserting individual cassettes, each of which contains a recording medium for storing a radiation image, and means for storing previously reserved data corresponding to each of the radiation images stored in the recording mediums, wherein the data, which finish the registration for reading, are displayed in the reading registration list.

(2) In the abovementioned apparatus, the cassette inserted in the slot can be identified in accordance with the correlation between the order of inserting cassettes and the order of touching screen by touching the predetermined position of the reservation data displayed on the displaying section after memorizing the order of inserting cassettes.

According to the abovementioned apparatus, it becomes possible to estimate a reading time required for a selected cassette beforehand by displaying a reading registration list listing data which finish the reading registration.

In addition, it becomes possible to improve maneuverability of the apparatus, by correlating the order of inserting cassette with the order of touching the screen.

(3) In the above configuration, the apparatus displays a warning message, when the reading registration is not processed within a predetermined period of time, after inserting the cassette 9.

(4) In the above configuration, the apparatus displays a warning message on the screen, when either the image outputting mode or the re-exposure mode is not selected within a predetermined period of time.

According to the abovementioned apparatus, it becomes possible that the warning message would bring the situation of no processing for the read image data over the predetermined period of time to the operator's notice.

In addition, erroneous correlative operations will be prevented, when another operator inserts another cassette while leaving the cassette unprocessed.

(5) In the above configuration, the read image and the reading registration list is displayed on the same screen with the reservation selecting list.

(6) In the above configuration, when the cassette is inserted in the slot, reservation selection is carried out from the upper order of the list.

According to the abovementioned apparatus, it becomes possible that an automatic reservation from the upper order of the list is achieved only by touching the reading reservation region on the screen.

In addition, maneuverability of the apparatus can be improved by displaying the read image on the same screen with the reservation selection list.

(7) The image reading apparatus, embodied in the present invention, comprises a plurality of slots for inserting cassettes, each of which contains a recording medium for storing a radiation image and means for previously reserving and storing data corresponding to each of the radiation images stored in the recording mediums, and stores the image data, which finish the reading registration among reserved data, into a memory means provided separately.

According to the abovementioned apparatus, it conveniently becomes possible to transfer the image data to other apparatus thereafter, and to conduct predetermined image processings, etc.

BRIEF DESCRIPTION OF THE DRAWINGS

The objectives and advantages of the present invention will become more apparent upon reading the following detailed description and upon reference to the drawings in which.

DETAILED DESCRIPTION OF THE PREFERRED EMBODIMENT

In the following, an exemplified embodiment of the present invention will be detailed, referring the drawings.

FIGS. 1(a) and 1(b) shows the structure of cassette embodied in the present invention. A whole housing of a cassette 9 is constructed with a back half casing 900 and a front half casing 901 (being the X-ray receiving surface) by fastening the peripheral edges with screws 902.

A peripheral edge of the cassette 9 is provided with an opening 903 from which a radiation image conversion plate 12 (hereinafter, for simplicity, referred to as the image conversion plate 12,) is accessible by drawing a cap 907. The image conversion plate 12 comprises a photo-stimulable phosphor layer, which stores energy in response to the amount of radiation penetrated through a subject after having been irradiated from a radiation source, to form a latent image in accordance with the distribution of the radial ray penetration rate. The photo-stimulable phosphor layer is formed on the image conversion plate 12 by means of vapor-phase accumulation or a coating application, and is further coated and/or shaded by a protective material, in order to prevent damage and harmful influences due to environmental conditions.

The image conversion plate 12 is placed on a rigid tray 904 located inside the cassette 9. A pair of stopping pins (not shown) penetrate the tray 904, in non-recorded regions of the image conversion plate 12.

The cap 907 incorporates a pair of locking mechanisms 908 which can be unlocked through a pair of locking holes 909. In addition, the cap 907 also incorporates a pair of sliding locks 910 by which the cap 907 can be opened or shut to withdraw or store the image conversion plate 12 with tray 904 from/in cassette 9.

An identification strip 911, which is stuck on the back surface of the cassette 9 and on which identification information printed in black and white is recorded, is utilized for detecting the sort and the size of the cassette 9 by reading the identification information. In addition, the identification strip 911 is also used to discriminate the mounting direction as well as the front or back surface of the cassette 9.

Although the top or bottom grid direction of the cassette 9 is designated by an arrow symbol 912, it is also possible to designate the top or bottom direction of the mounting cassette 9 in such a manner that the cap 907 is inserted with its lower side down.

A clip 913 is mounted on the back half of the casing 900 to hold diagnostic records, etc. by gripping them between the paper clip 913 and a concave region 900a, which is formed under the paper clip 913 on the back half of the casing 900.

Figure 2:
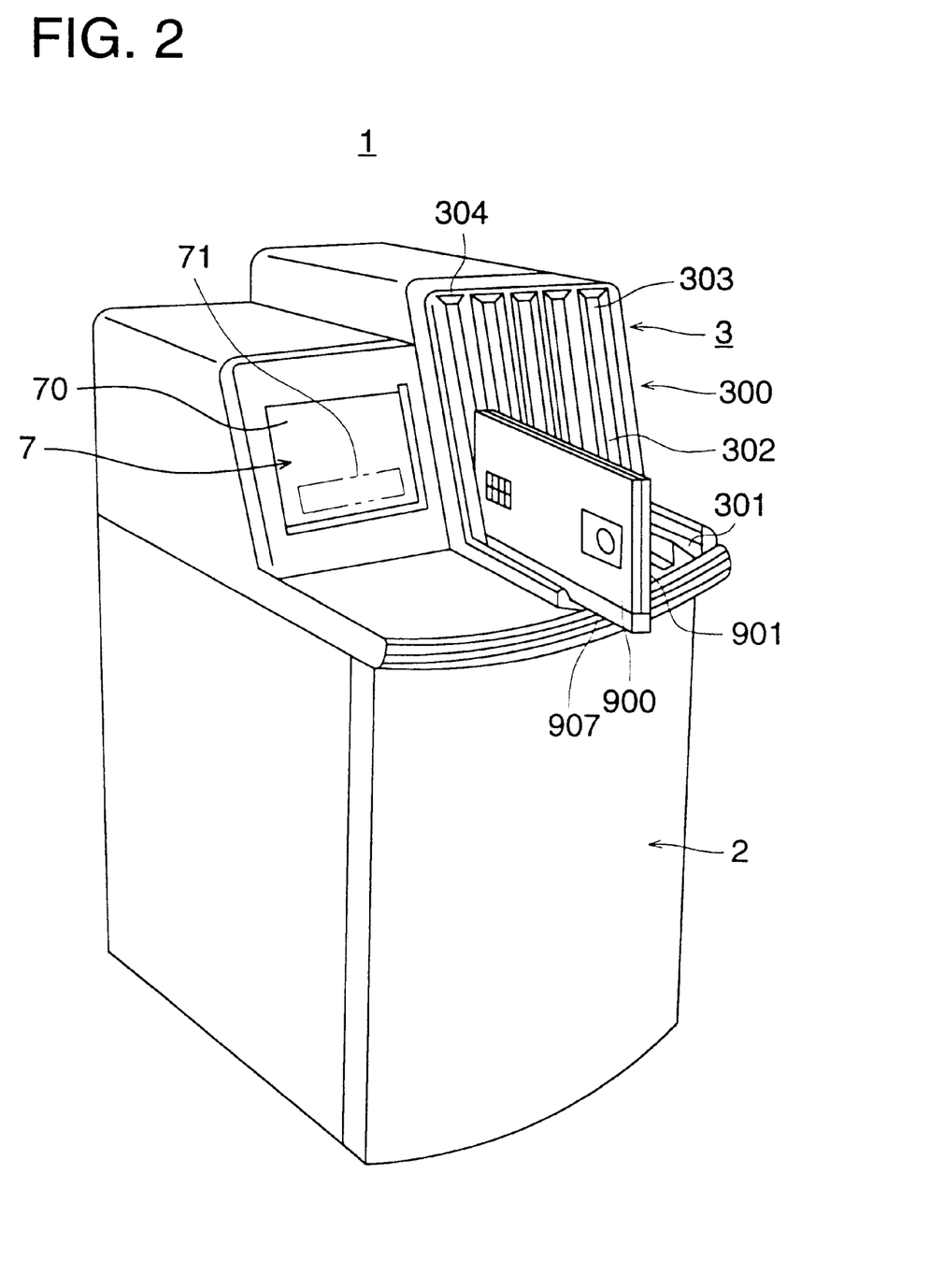
FIG. 2 shows an example of a structural perspective view, illustrating the outward appearance of an image reading apparatus embodied in the present invention.

FIG. 2 shows the structural exterior of the image reading apparatus 1, embodied in the present invention. A cassette stacking section 3 and a display/operation section 7 are located substantially in parallel at an upper side of the image reading apparatus 1. Specifically, the cassette stacking section 3 is disposed at a right side toward upper direction of the image reading apparatus 1, while the display/operation section 7 is disposed at a left side toward upper direction of the image reading apparatus 1.

The cassette stacking section 3 comprises a inserting section 300 provided every five slots. The display/operation section 7 comprises a CRT display section, and a touch panel 71 mounted on the CRT display screen, serving as a operating section, to conduct such operations as reservation for medical inspection, patient registration, status setting of the apparatus, etc. and is also used to display the status of various sections in the apparatus as well as the radiation image being read by the apparatus.

Operating instructions can be inputted by pushing the touch panel 71 of the display/operation section 7, for which, e.g., a 15 inches CRT display apparatus (24 bits for color, 256 gradations for monochrome, at a resolution of 1024× 768) is utilized.

The touch panel 71 of the present embodiment employs an optical method, which responds by shading a light, e.g., an infrared beam. The inserting section 300 comprises an inserting guide 301 and a storing section 302. The inserting guide 301 has channels leading to the storing section 302, so as to guide the cassette 9 to the storing section 302 in a state of the vertical position. In the storing section 302, the cassette 9 is stored, maintained at a predetermined space from the adjacent cassette.

The cassette 9 is inserted in a vertical position, basing on the front side of the apparatus in a state that a longer side direction of the cassette 9 is a horizontal position. Immediately after the cassette 9 is inserted in the storing section 302, a shading shutter 303, which is mounted on every slot at the opening of the storing section 302, closes, so that no light can leak into the opening.

Although it is possible to withdraw the cassette 9 from every slot, LED lamps 304, which designate a reading status, are mounted on the top of every slot to prevent erroneous withdrawal of the cassette 9. Incidentally, the size of the cassette 9 is not necessarily uniform, but can vary in a plurality of sizes.

Figure 3:
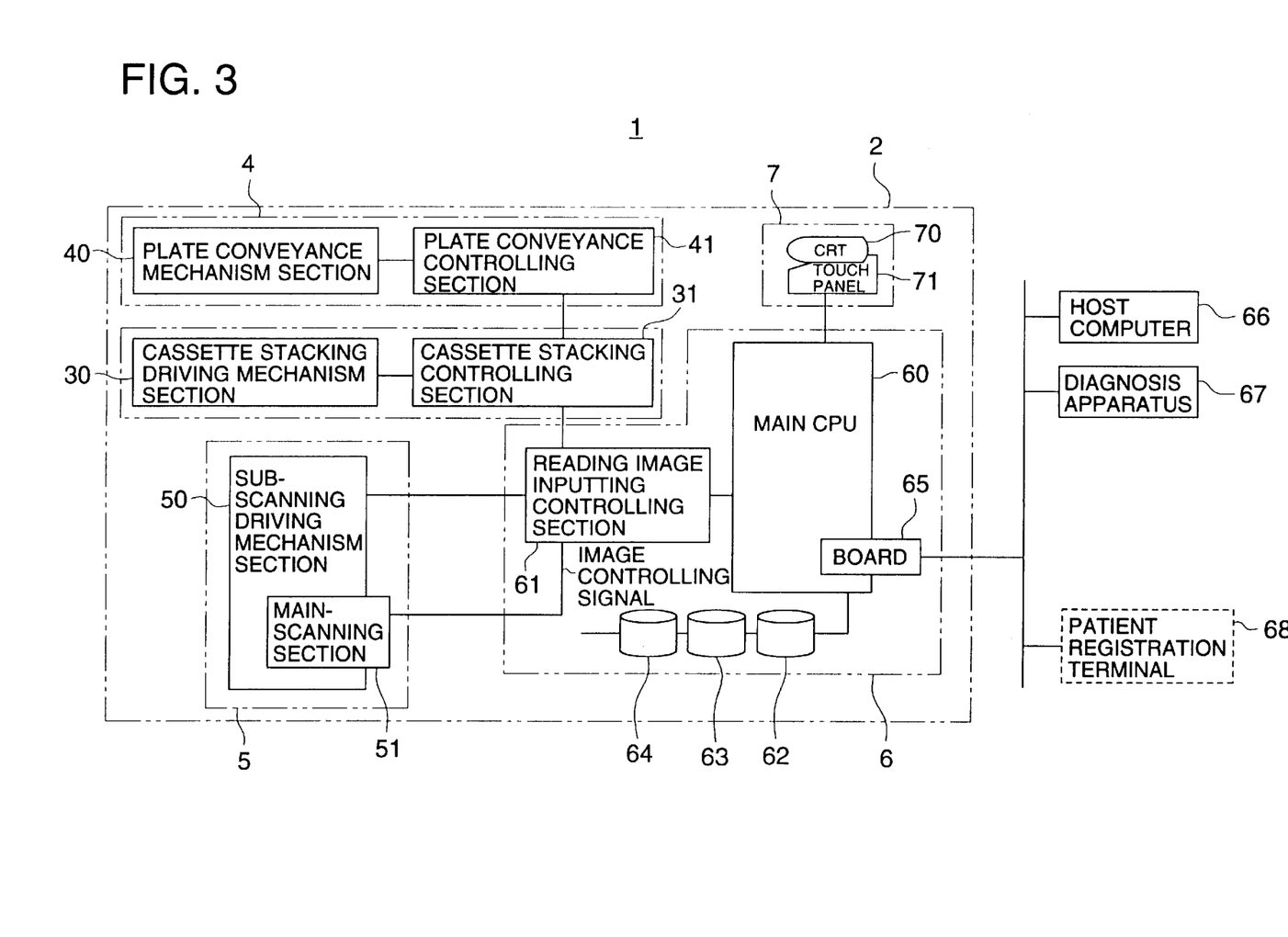
FIG. 3 shows a block diagram of an image reading apparatus embodied in the present invention.

FIG. 3 shows a block diagram of a radiation image reading apparatus, embodied in the present invention.

The cassette stacking section 3, which is provided in a main frame 2 of the image reading apparatus 1, comprises a cassette stacking section driving mechanism section 30 (hereinafter, for simplicity, referred to as the stack driving mechanism 30) and a cassette stacking section controlling section 31 (hereinafter, for simplicity, referred to as the stack controller 31), and is capable of setting the cassette 9 which contains a radiation image conversion plate and varies in a plurality of sorts. When the cassette 9, containing a radiation image converting plate, is inserted into the slot, it is set in a predetermined state, by means of the stack driving mechanism 30, basing on the controlling actions of the stack controller 31.

A plate controlling section 4 comprises a plate conveyance section driving mechanism section 40 (hereinafter, for simplicity, referred to as the plate conveyance mechanism 40) and a plate conveyance section controlling section 41 (hereinafter, for simplicity, referred to as the plate conveyance controller 41). The plate conveyance controller 41 controls the plate conveyance mechanism 40, based on the instructions sent from the stack controller 31. Then, the plate conveyance mechanism 40 withdraws the image conversion plate 12 from the inserted cassette 9 and conveys it to an image reading section.

In the image reading section 5, a sub-scanning section driving mechanism 50 (hereinafter, for simplicity, referred to as the sub-scanning mechanism 50) and a main-scanning section 51 are provided for reading images, wherein a laser beam emitted from the main-scanning section 51 scans in the main-scanning direction while shifting the main-scanning section 51 in the sub-scanning direction by means of the sub-scanning mechanism 50.

A system controlling section 6 comprises a main CPU 60 and a reading section image inputting controlling section 61 (hereinafter, for simplicity, referred to as the image inputting controller 61). To control the whole system as well as an image processing, an image outputting and an image administration, the ports of the main CPU 60 are connected with such devices as a system disk 62 for storing system programs, image disks 63 and 64 for storing digital image data, a host computer through a board 65, a diagnosis apparatus and a patient registration terminal. Further, to read the image stored in the image conversion plate 12, the image inputting controller 61 controls the stack controller 31, the sub-scanning mechanism 50 and the main-scanning section 51, and sends the image data to the main CPU 60.

The display/operation section 7 comprises the CRT display section 70, which serves as the display section to display images read by the image reading section 5, and the touch panel 71, which is mounted on the CRT screen and serves as the operating section, wherein instructions input by the touch panel 71 are transmitted to the main CPU 60 to perform necessary controlling actions on the basis of the inputted instructions.

Next, the performance of the apparatus, embodied in the present invention, will be detailed in the following.

Figure 4:
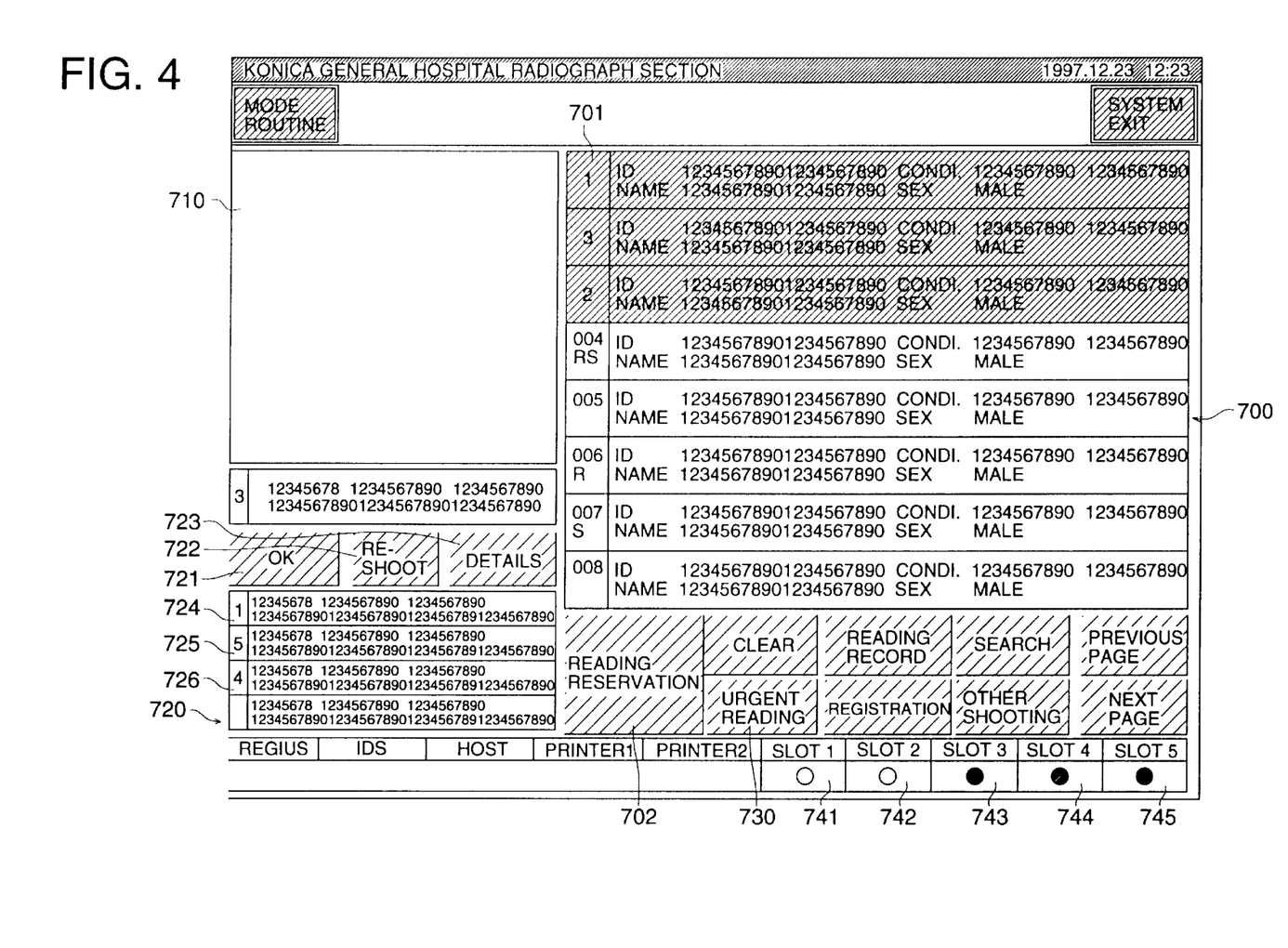
FIG. 4 shows an example of the layout displayed by the image reading apparatus embodied in the present invention.

FIG. 4 shows an example of text displayed by the display section in the display/operation section 7. In FIG. 4, numerals 700, 710, 720 designate a reservation information list, an image displaying section and a reading registration list, respectively. In the reading registration list, numerals 3, 1, 5, 4 located at the left designate the slot numbers. Hereinafter, the reading registration is to correlate the order of registration with the order of display on the list. The data, scheduled to be read, is displayed in the reservation information list 700, and the data, scheduled to perform image reading, are stored in a memory means. The reservation information list 700 is displayed under the touch panel 71 shown in FIG. 2 and numerals in the list shows the number of usable characters.

Figure 1:
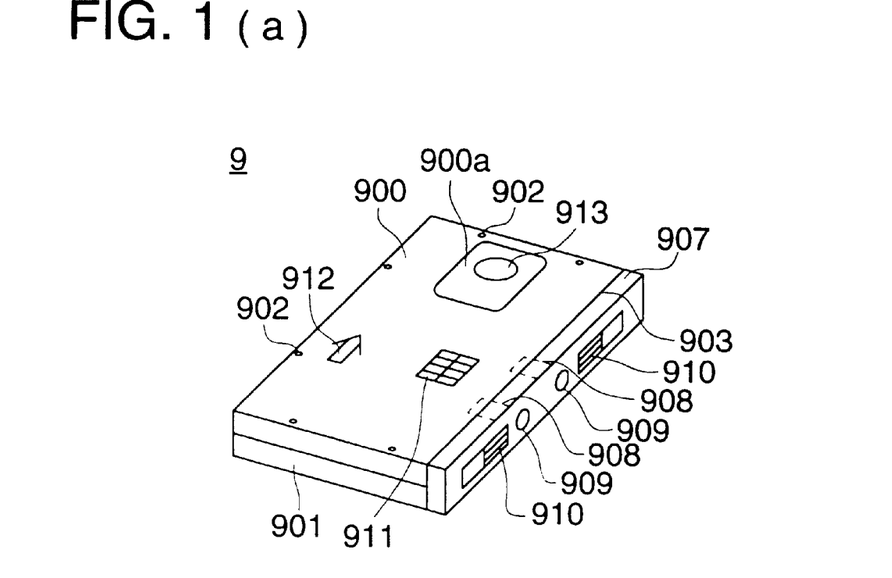
FIGS. 1(a) and 1(b) shows an example of a structural perspective view of a cassette.

When the plural sorts of cassettes 9 with stored image are inserted into the cassette stacking section 3, the operator could arbitrarily insert them into any slot, since the main CPU 60 memorizes the numbers of cassettes 9 being inserted. At this time, the main CPU 60 reads the information printed on the identification strip 911, stuck on the surface of cassette 9 (shown in FIG. 1), to designate the size and type of each inserted cassette.

Therefore, when the operator successively inserts the cassettes 9 in the arbitrary slots, the main CPU 60 reads the information regarding into which slot any specific cassette 9 is inserted, the sequence of inserting and the size of the cassette 9.

Figure 5:
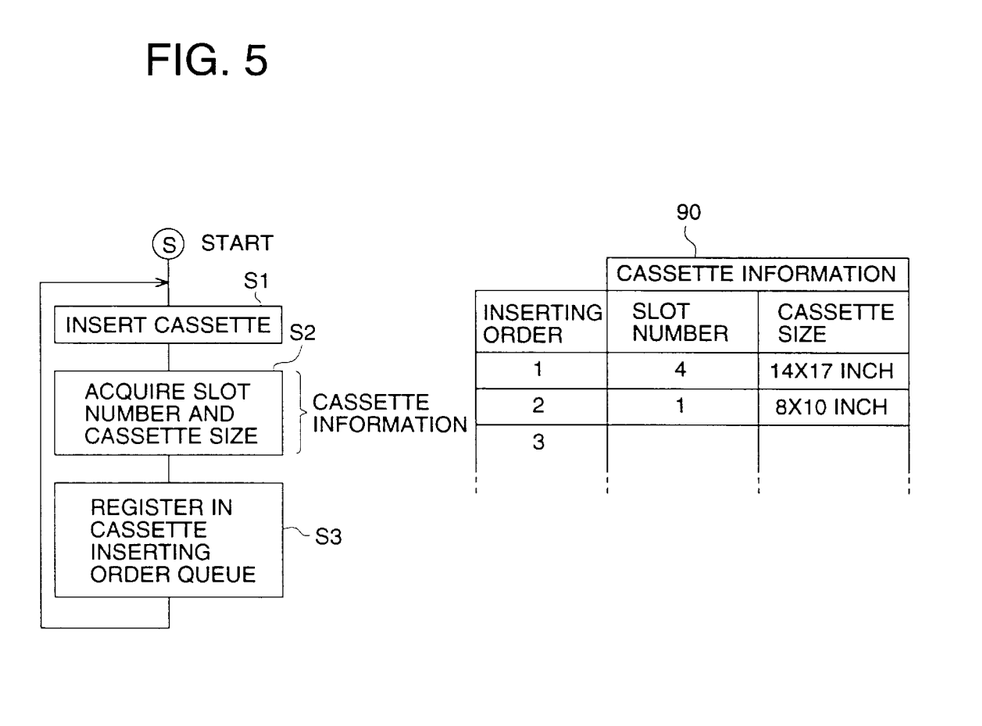
FIG. 5 shows a flow chart of the cassette inserting operation.

FIG. 5 shows a flow chart of the cassette inserting operation.

When the operator inserts a cassette 9 into the cassette stacking section 3 (S1), the main CPU 60 reads the code printed on the identification strip 911, stuck on the surface of cassette 9 (shown in FIG. 1), to obtain the slot number, into which the cassettes 9 is inserted, and the size of the inserted cassette.

Then, the main CPU 60 registers each of the read cassette information into a cassette inserting order queue 90 (hereinafter, for simplicity, referred to as the inserting queue 90). In FIG. 5, the numeral 90 designates the inserting queue 90 which comprises an inserting order, information for specifying the slot, e.g., slot numbers and cassette sizes including such as 14×17 inch size, 8×10 inch size or information for showing size, and is stored, e.g., in the image disk 63 or 64.

Figure 6:
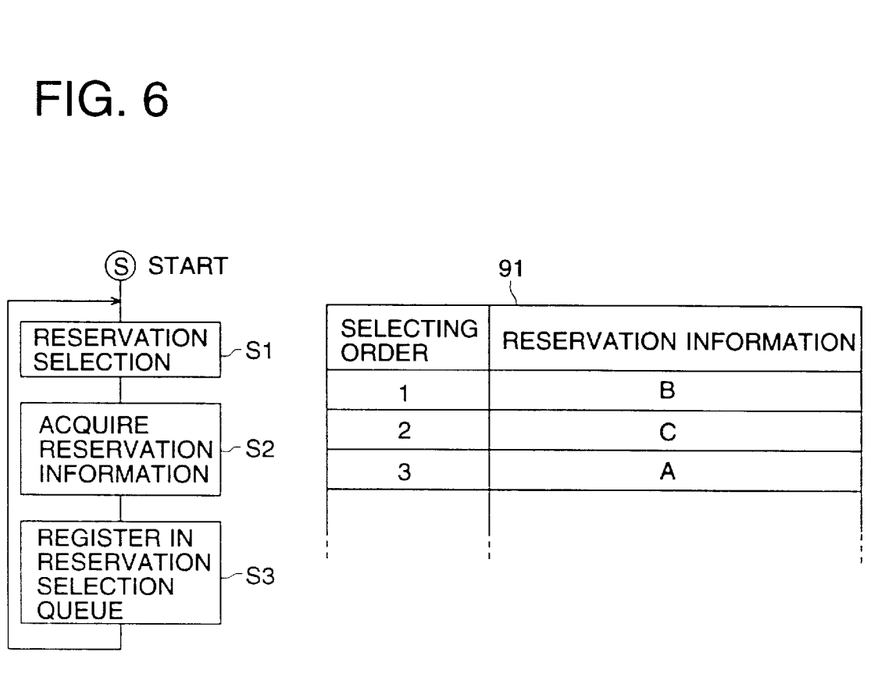
FIG. 6 shows a flow chart of the reservation selection operation.

FIG. 6 shows a flow chart of the reservation selecting operation.

Initially, the operator selects an item to be reserved from items in the reservation information list 700 by pushing the corresponding region on the CRT screen (S1). Then, a numeral 1 is displayed at a region of a number displaying column 701, which corresponds to the name line of the first touch, shown in FIG. 4.

If the operator touches a name line next other of the first touch, a numeral 2 is displayed at a corresponding region of the number displaying column 701, which designates the second touch, and successive touches as well. Incidentally, characters "R" and "S" displayed on the number displaying column 701 designate a reference suspension and an inspection suspension, respectively. Although, in a normal mode, images must be memorized by touching a OK region 721, in the case of either "R" or "S", image outputting is disabled and image data is not erased until the inspection suspension is canceled.

Next, the main CPU 60 obtains the selected reservation information (S2), and registers them in a reservation selecting queue 91 (S3). As shown in FIG. 6, the reservation selecting queue 91 includes a selection order and reservation information, and is stored, e.g., in the image disk 63 or 64.

Figure 7:
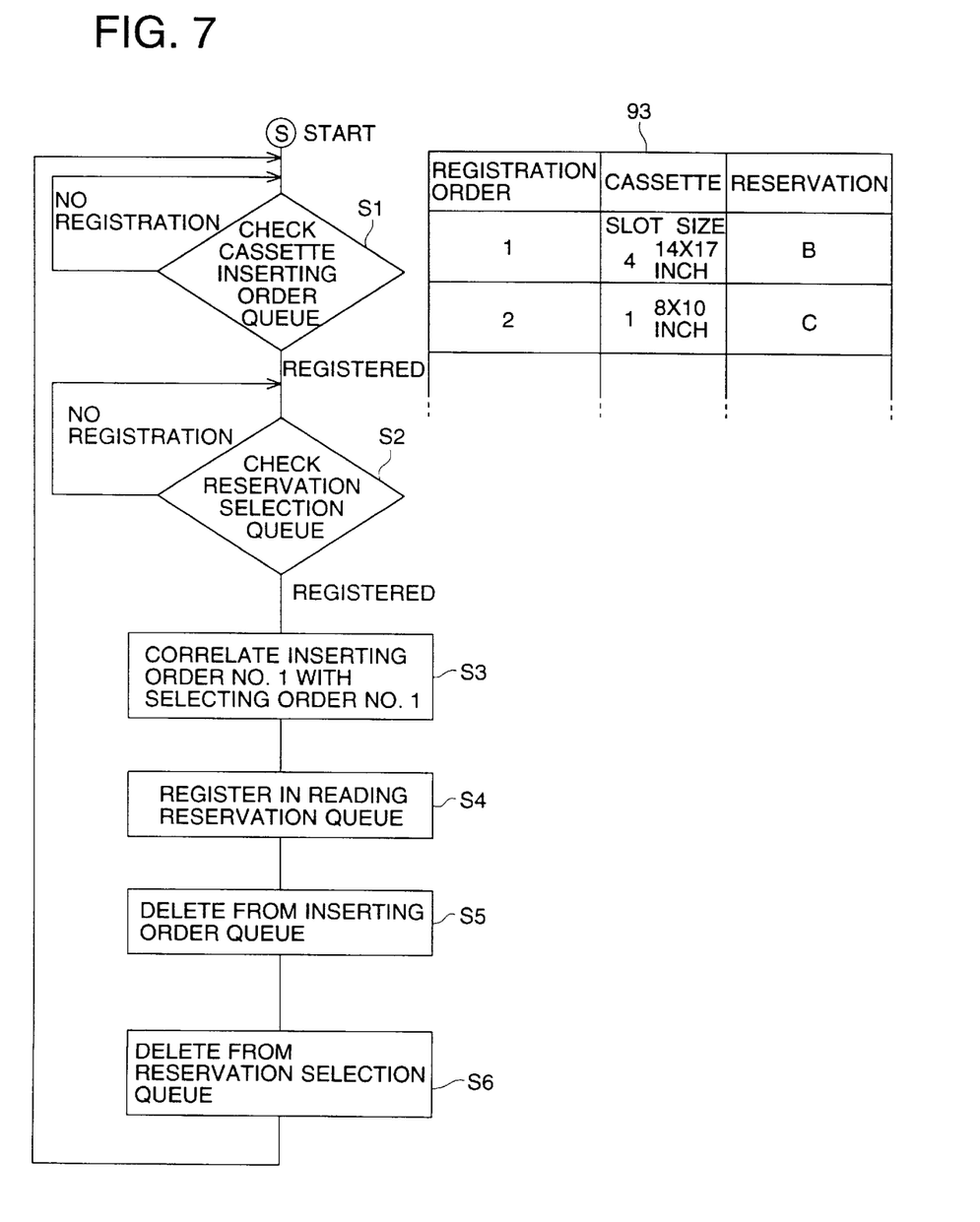
FIG. 7 shows a flow chart of the reading registration operation.

Subsequently, the operator touches a reading reservation region 702 to start the reading operation. FIG. 7 shows a flow chart of the reading registration operation (correlating the cassette with its reservation). The main CPU 60 checks the inserting queue 90, in which slot numbers and cassette sizes are stored in accordance with the inserting order, and then checks the reservation selecting queue 91 when the main CPU 60 determines that the cassette is registered in the inserting queue 90.

When the main CPU 60 determines that the cassette is registered in the reservation selecting queue 91, the main CPU 60 correlates the first inserting order with the first selecting order (S3), and then, registers the correlated result in a reading registration queue 93 (S4), in which slot numbers, cassette sizes and reservation information are stored in accordance with the registering order, as shown in FIG. 7. According to this reading registration queue 93, it is shown that the first registered cassette is inserted into the slot 4, and its cassette size is 14×17 inch, and its reservation information is B.

After finishing the registering operation into the reading registration queue 93, the main CPU 60 deletes data of the registered cassette from the inserting queue 90 (S5), as well as from the reservation selecting queue 91 (S6). Then, the main CPU 60 returns to the first step of the flow chart to repeat the same operations as mentioned above.

As a result, the patient data, specified by the foregoing operations, is finally confirmed, and transferred to the reading registration list 720. Then, the image displaying section 710 displays the image of the first registered patient's name, and successively displays images in accordance with their registering order. In other words, the main CPU 60 performs the image reading of the cassette 9, inserted in the cassette stacking section 3, in accordance with the registering order of the cassette 9.

The radiation images are read by the apparatus main frame 2, under control of the main CPU 60, and the image data are transferred to the image displaying section 710 to successively display the radiation images of the specific patient name in accordance with the registering order. After finishing the observation of the images, the operator touches a OK region 721 of the screen to finally fix the displayed image and to enable the process of outputting the image data and/or storing the image data in a memory means.

After touching the OK region 721, the image data of No. 1, which designates the number of slot 1, is scrolled up, and displayed on the image displaying section 710. If the displayed image is not in a good state, the operator would touch a re-exposure region 722 on the screen to return its image data to the reservation information list 700. In addition, the operator can acquire further detailed image data by touching a detail region 723 of the screen.

According to the present invention, it becomes possible to estimate a reading time of a specific cassette beforehand, since the data, registered in the reservation information list 700, are transferred in the order of registration to the reading registration list 720 which is displayed in a reduced size, so that the operator can easily perceive the order of image direading Incidentally, it is also possible to store the image data, after completing the reading registration, into a separately provided memory means without actually displaying them on the displaying section. Accordingly, it is conveniently possible to transfer the image data to other apparatus thereafter, and to conduct predetermined image processings, etc.

Figure 8:
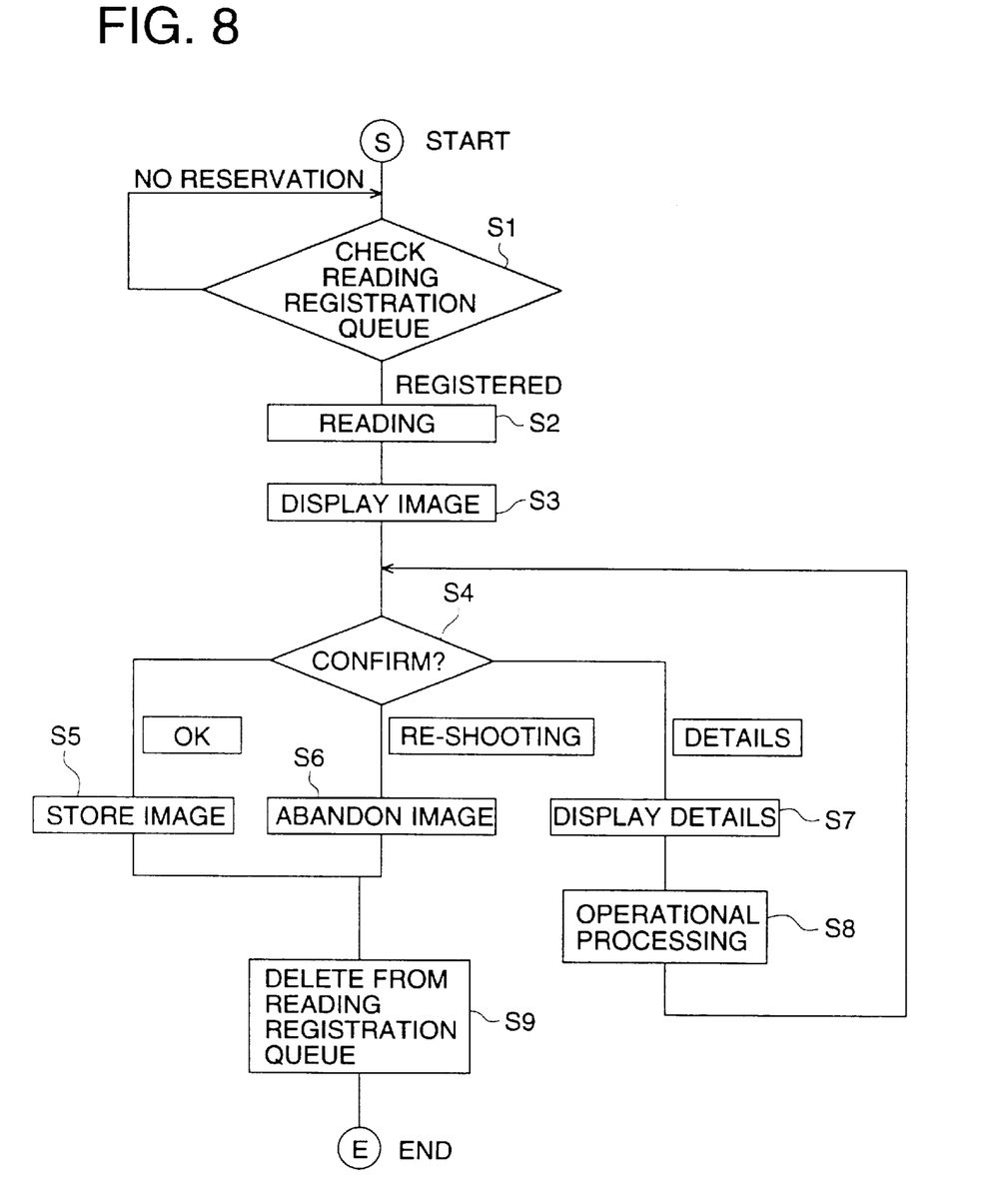
FIG. 8 shows a flow chart of the image reading operation.

FIG. 8 shows a flow chart of an image reading operation. Initially, the main CPU 60 checks the reading registration queue 93 (S1). When the main CPU 60 determines that the cassette is registered in the reading registration queue 93, the reading action is carried out (S2), and the read image is displayed on the image displaying section 710 (S3).

Next, the main CPU 60 checks which region was touched by the operator (S4). When the OK region 721 is touched, the image data is stored (S5), and deleted from the reading registration queue 93 (S9). When the re-exposure region 722 is touched, the image data is abandoned (S6), and deleted from the reading registration queue 93. When the detail region 723 is touched, details are displayed (S7), and the operator would perform processing operations, which could include an enlarged display of the image, a change of image processing, etc. and returns to the step 4 thereafter.

During the abovementioned image reading operation, a warning message can be displayed on the screen, when either the image outputting mode or the re-exposure mode is not selected within a predetermined period of time. As a result, the warning message would bring the situation of no processing for the read image data over the predetermined period of time to the operator's notice.

Further, it is also possible to display a warning message, when the reading registration is not processed within a predetermined period of time, after inserting the cassette 9. As a result, the warning message would bring the situation of leaving the cassette 9 unprocessed to the operator's notice.

In addition, it is also possible to display a warning message, when the reading registration is not processed within a predetermined period of time, after selecting a specific reservation. As a result, this will prevent erroneous correlative operations, such as when another operator inserts another cassette 9, while leaving the current cassette 9 unprocessed.

Furthermore, it is possible to display the read image and the reading registration list on the same screen with the reservation selecting list, in order to improve the ease of operation of the apparatus.

As described in the above, according to the apparatus embodied in the present invention, it is possible to improve the ease of operation of the apparatus by correlating the order of inserting the cassettes 9 with the order of touches of the display screen.

The scope of the present invention is not limited to the abovementioned embodiment in which the order of inserting the cassettes 9 is correlated with the order of touches of the display screen. Also included in the scope of the present invention, for example, is another embodiment in which the reservation can be automatically selected from the top of the list every time a new cassettes 9 is inserted. In this case, an automatic reservation from the top of the list is achieved merely by touching the reading reservation region 702 on the screen.

In addition, although a touch screen is employed for selecting reservation data, etc. in the abovementioned embodiment, a keyboard, a mouse, etc. are also acceptable for this purpose to embody the present invention.

Next described in the following, is an urgent reading processing mode, which is urgently requested in emergency cases, etc., during the radiation image reading apparatus is in the reservation reading mode.

Figure 10:
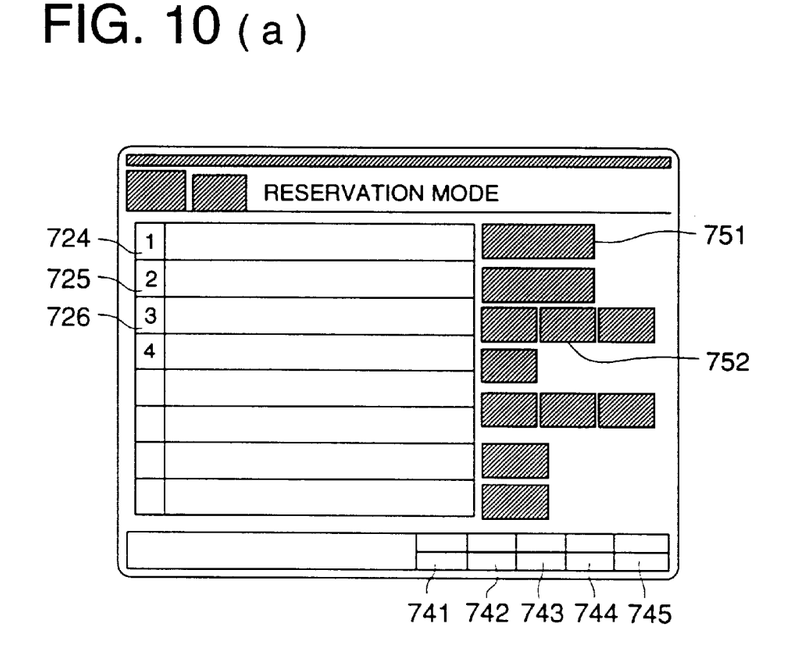
FIGS. 10(a) and 10(b) show exemplified layouts displayed by the image reading apparatus embodied in the present invention.

The urgent reading mode is selected by touching an urgent switch 752 shown in FIGS. 10(*a*) and 10(*b*) or an urgent reading switch 730 shown in FIG. 4, which flashes on and off after touching, to notify that the radiation image reading apparatus enters in the urgent reading mode.

When the cassette under urgent reading is inserted into the cassette stacking section 3, an urgent mark written in the identification strip 911 is read at the time of reading the identification strip 911 to recognize the cassette under urgent reading. In addition, when the urgent reading mode is selected, a reservation information reference/modification screen is displayed on the CRT display section 70, so that the operator can input predetermined items by touching the screen.

Incidentally, it is a possible configuration that the apparatus automatically enters in the urgent reading mode, when detecting the urgent mark written on the identification strip 911. In this configuration, the apparatus can enter in the urgent reading mode by merely inserting the cassette under urgent reading, instead of touching the urgent switch 752 or the urgent reading switch 730 every time the urgent reading is necessary. Alternatively, it is also possible that the color, e.g., the side surface color, of the cassette under urgent reading is different from that of the cassette for reservation reading use to discriminate them.

Further, since the reading status of the cassette is displayed on the reading status displaying region 741–745 every slot of the storing section 302 at the time when the cassette under urgent reading is inserted into the storing section 302 of the cassette stacking section 3, it is possible that the cassette under urgent reading is quickly and accurately loaded onto the slot of the storing section 302 by recognizing the reading status of the cassette inserted into each slot.

Figure 9:
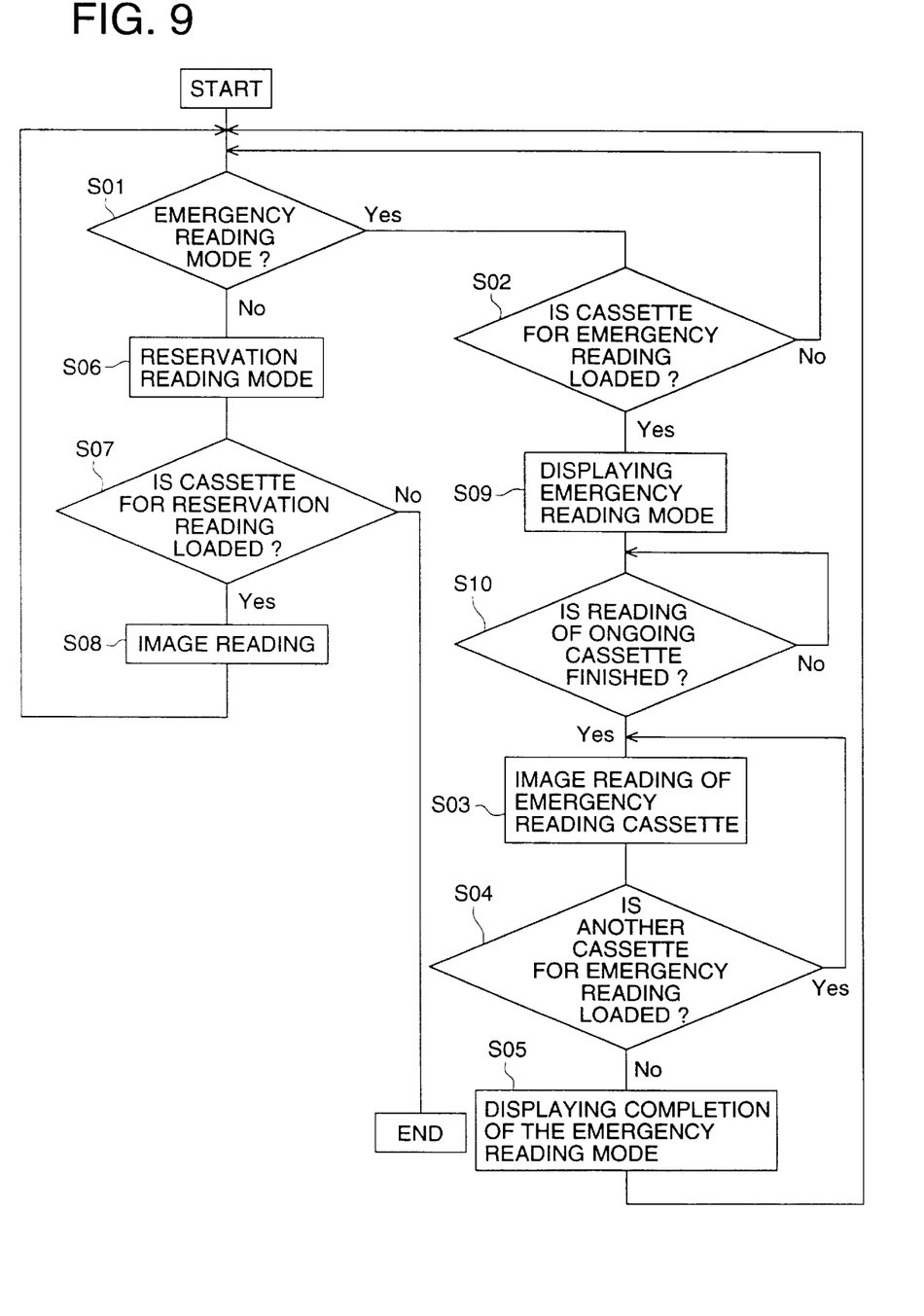
FIG. 9 shows a flow chart of the urgent reading operation.

Referring to the flow chart of the present embodiment shown in FIG. 9, reading processing in urgent reading mode, which can override the reservation reading mode and reading reservations, will be detailed as follow.

As mentioned above, the apparatus detects whether the processing status is in the urgent reading mode or not (S01), by checking the urgent switch 752 or the urgent reading switch 730, etc. When the apparatus determines that the processing status is in the urgent reading mode, the apparatus checks whether the cassette under urgent reading is loaded onto the cassette stacking section 3 or not (S02). When loaded, the apparatus flashes the urgent switch 752 or the urgent reading switch 730 on and off in a red color to display the urgent reading mode (S09), and urgently conducts necessary processings for image reading of the urgent cassette (S03), after the operation of inputting predetermined items as mentioned above and the finish of the image reading operation for the ongoing cassette (S10). If another urgent cassette is loaded, the urgent reading mode is successively performed for the next urgent cassette (S04). If no urgent cassette is loaded, the apparatus stops flashing of the urgent switch 752 or the urgent reading switch 730 to display the finalization of the urgent reading mode (S05). Alternatively, warning sound generated by buzzer, etc. can be employed to notify the finalization of the urgent reading mode.

Then, the apparatus returns to the step S01 of detecting whether the processing status is in the urgent reading mode or not (S01), and if not, enters into the reservation reading mode (S06). When the cassette of reservation reading is loaded (S07), the apparatus performs the image reading processing of the loaded cassette (S08), or if not, finalizes the reading processing. After finalizing the reading processing of the cassette of reservation reading, the apparatus returns to the step S01 again.

According to the reading processing of the present embodiment mentioned above, since the apparatus detects whether the processing status is in the urgent reading mode or not, every time when the reading processing mode of each cassette is finalized, reading processing of the cassette under urgent reading can override that of the cassette registered in the reading reservation. Therefore, according to the radiation image reading apparatus embodied in the present invention, it becomes possible to quickly cope with urgent reading processing in cases of urgent diagnosis for an emergency patient, etc.

Further, according to the radiation image reading apparatus shown in FIG. 2, which can perform reading processing in order after loading a plurality of cassettes, since reading processing in the urgent reading mode is always performed after the finish of image reading operation for the ongoing cassette in the reservation reading mode, there is no erroneous mixture of reading processings between both modes.

Figure 11:
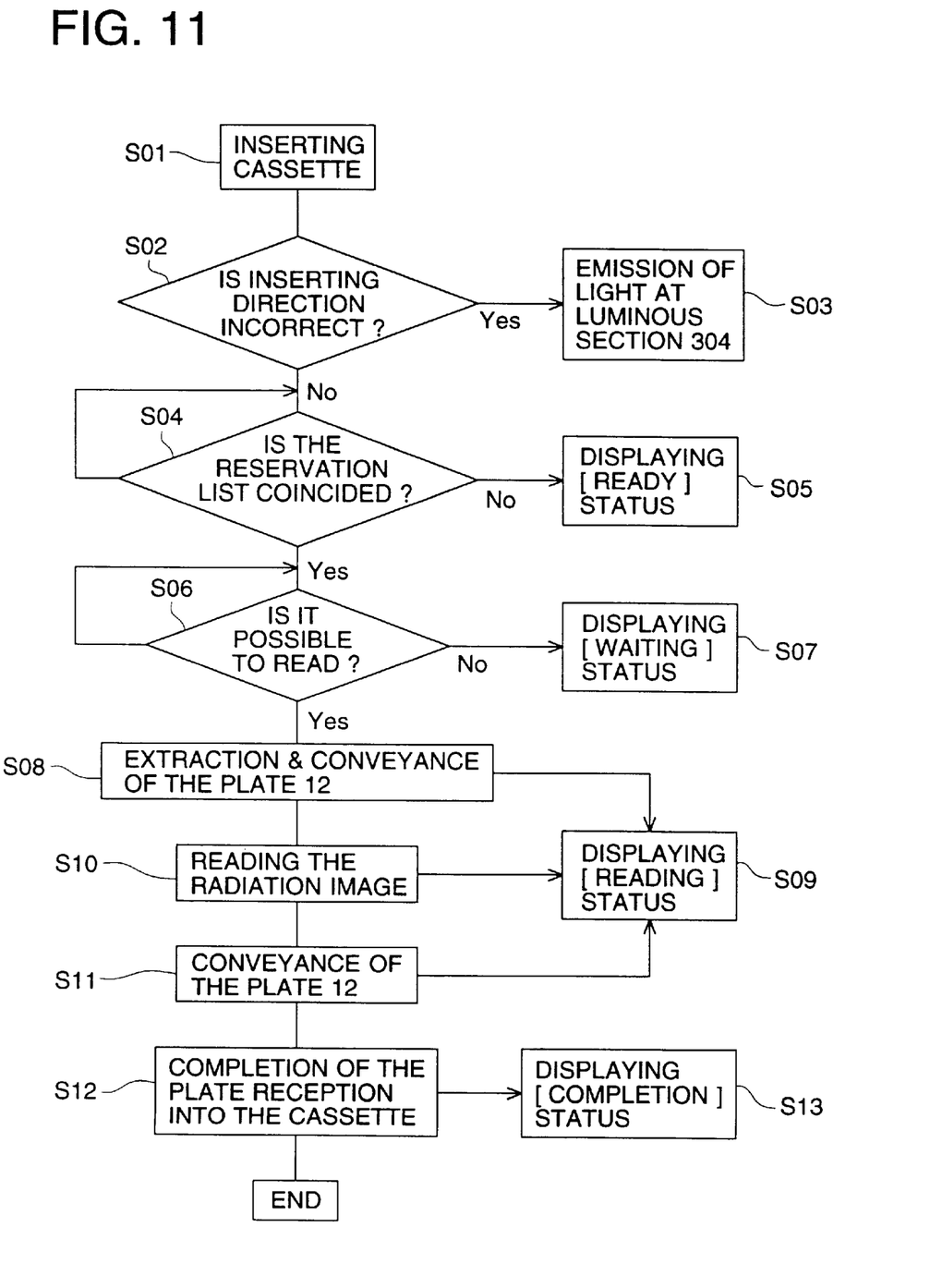
FIG. 11 shows a flow chart of the image reading operation including display of the reading status.
Figure 12:
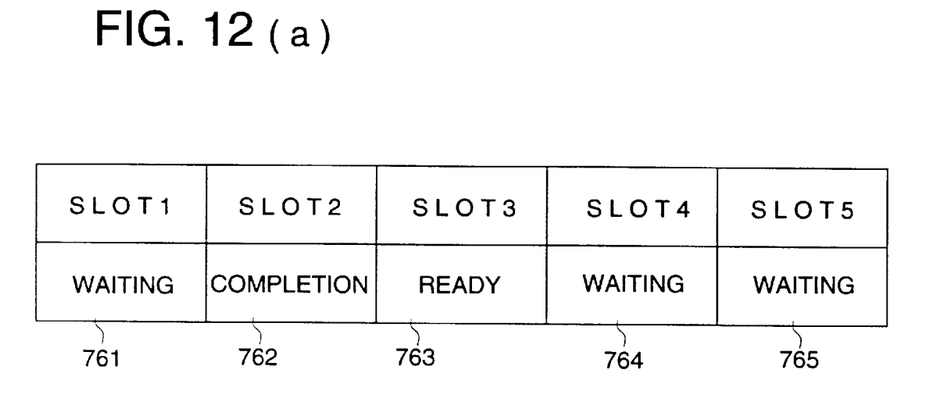
FIGS. 12(a) and 12(b) show an exemplified embodiment of the reading status display regions.

Referring to FIG. 11 and FIGS. 12(a), and 12(b) the display actions pertaining to the reading status will be described in the following.

The reading status display regions 741, 742, 743, 744 and 745, which display reading status of each cassette and are corresponding to each of slots 311, 312, 313, 314 and 315 of the storing section 302 respectively, is located at the lower portion of the screen as shown in FIG. 10(a), FIG. 10(b) and FIG. 4. Each of display regions 741–745 is comprised of a slot number sign of [SLOT 1]–[SLOT 5], which is corresponding to each slot 311–315, and a luminous part located under the slot number sign. The luminous part can flash on and off, and can change its luminous color, such as yellow, green, blue, white, red, etc., so that each color corresponds to each reading status, such as [READY], [READING], [COMPLETION], [WAITING] and [TROUBLE]. For example, a red color or a flashing of the luminous part would designate a troubling status of the reading process. Incidentally, the extraction of the cassette inserted into the slot is banned during the reading processing, while it is possible to extract the cassette in the state of [COMPLETION], [WAITING] or [TROUBLE].

Referring to the flow chart of the present embodiment shown in FIG. 11, the cassette reading status displaying actions of the reading status display regions 741–745 will be described as follow, in accordance with each step of the reading processing.

When the cassette 9 is loaded onto the storing section 302 of the cassette stacking section 3 through the slot (S01), the apparatus checks whether the inserting direction of the cassette 9 is correct or incorrect (S02), by detecting the identification strip 911 of the cassette 9. If incorrect, the luminous section 304 of the corresponding slot emits a light (S03).

When the apparatus determines that the inserting direction of the cassette 9 is correct, the apparatus checks whether the patient ID number coincides with the reservation list or not (S04), by reading the patient ID number written on the identification strip 911 of the cassette 9. If not, the display region emits a light in a color corresponding to [READY] to display the [READY] status (S05), until the patient ID number coincides with the reservation list. When the apparatus determines that the patient ID number coincides with the reservation list, the apparatus checks whether the cassette is possible to read or impossible (S06). If impossible, the display region emits a light in a color corresponding to [WAITING] to display the [WAITING] status (S07).

When the apparatus determines that the cassette is possible to read, the radiation image conversion plate 12 is extracted from the cassette 9 located at the storing section 302 in the apparatus, and is conveyed to the image reading section 5 (S08). In the image reading section 5, the apparatus reads the radiation image stored in the radiation image conversion plate 12 (S10), and then conveys the radiation image conversion plate 12 back to the cassette 9 (S11). During the steps of S08–S11 mentioned above, the display region emits a light in a color corresponding to [READING] to display the [READING] status (S09). When the reception of the radiation image conversion plate 12 into the cassette 9 is completed (S12), the display region emits a light in a color corresponding to [COMPLETION] to display the [COMPLETION] status (S13). For this feature, the operator can recognize the completion of reading processing. In addition, the operator can recognize the reading status of every steps during the cassette reading processing by means of each color displayed on the display region.

Since the reading status display regions 741–745 are arranged on the screen of the CRT display section 70 as mentioned above, the operator can recognize the status of reading processing while watching the other information displayed on the same screen, such as reservation list, etc. Therefore, it becomes possible for operator to successively prepare the cassettes for image reading by drawing the completed cassette and loading the next cassette, and to conduct quick reading processing and operation by obtaining the other information displayed on the same screen. Further, in the present embodiment, it is convenient for the operator to recognize the reading status either near the CRT screen or remote from the CRT screen, since the reading status can be also displayed on the luminous section 304 located at each of slots 311–315.

Furthermore, the quick reading processing and operation can be maintained even if a plurality of cassettes are loaded onto the apparatus for reading processing, since the reading status of each cassette can be monitored by the operator. Since the reading order of a plurality of cassettes and the reading status of them can be separately displayed on the display sections 724, 725, 726 and on the reading status display regions 741–745, respectively, as shown in FIG. 4, the operator can recognize the next cassette to be read, even if a plurality of loaded cassettes are waiting the reading processing. In addition, it is also possible for the operator to input new information for the reading processing, while confirming the reading status of the cassette, by means of the touch panel, serving as the inputting means, mounted on the CRT display section 70. These facts will further facilitate the quick reading processing and operation.

Next, another example of the reading status display section will be described as follow, referring FIGS. 12(a) and 13(b).

Each of the reading status display sections 761, 762, 763, 764 and 765, shown in FIGS. 12(a) and 12(b), displays the reading status with characters, such as [COMPLETION], etc., located under the slot numbers signs of [SLOT 1]–[SLOT 5], corresponding to each slot of the storing section 302 of the cassette stacking section 3. In the exemplified embodiment shown in FIG. 12(a), the reading status display sections 761, 762, 763, 764 and 765 are displaying the reading status of [WAITING], [COMPLETION], [READY], [WAITING] and [WAITING], respectively.

On the other hand, FIG. 12(b) shows a case that the reading status display section 763 is displaying the reading status of [READING] when the cassette loaded onto the slot 313 enters the reading possible status from the ready status. In case of a trouble occurrence, the characters of [TROUBLE] can be displayed, optionally associating with the flashing on and off.

As mentioned above, according to the example shown in FIGS. 12(a) and 12(b), it becomes possible for the operator to immediately recognize the reading status, since it is displayed by the characters being directly readable.

According to the present invention, the following functions can be attained:
(1) Since the image reading apparatus, embodied in the present invention, is comprised of a plurality of slots for inserting cassettes, each of which contains a recording medium for storing a radiation image and means for previously reserving and storing data corresponding to each of the radiation images stored in the recording mediums, and displays the reading registration list listing data which finish the reading registration from among the reserved data, it becomes possible to estimate the reading time required for a selected cassette.
(2) Since the image reading apparatus, embodied in the present invention, is structured so that the cassette inserted in the slot can be identified in accordance with the correlation between the inserting order of cassettes and the touching order on the screen by touching the predetermined positions of the reservation data displayed on the displaying section, after memorizing the inserting order of cassettes, it becomes possible to improve ease of operation of the apparatus.
(3) During the image reading operation, a warning message can be displayed on the screen, when either the image outputting mode or the re-exposure mode is not selected within a predetermined period of time. As a result, it becomes possible that the warning message would bring the situation of no processing for the read image data over the predetermined period of time to the operator's notice.

In addition, it is also possible to display a warning message, when the reading registration is not processed within a predetermined period of time, after inserting the cassette 9. As a result, it becomes possible that the warning message would bring the situation of leaving the cassette 9 unprocessed to the operator's notice.
(4) The ease of operation of the apparatus can be improved by displaying the read image and the reading registration list on the same screen along with the reservation selecting list.

In addition, erroneous correlative operations can be prevented when another operator inserts another cassette 9 while leaving the current cassette 9 unprocessed, since the apparatus displays a warning message, when the reading registration is not processed within a predetermined period of time, after selecting a specific reservation.
(5) Since the image reading apparatus, embodied in the present invention, comprises a plurality of slots for inserting cassettes, each of which contains a recording medium for storing a radiation image and means for previously reserving and storing data corresponding to each of the radiation images stored in the recording mediums, and stores the image data, which finish the reading registration among reserved data, into a separately provided memory means, it becomes conveniently possible to transfer the image data to other apparatus thereafter, and to conduct predetermined image processings, etc.
(6) When a cassette is inserted into a slot, it becomes possible that an automatic reservation from the top of the list is achieved by merely touching the reading reservation region on the screen, since the reservation can be automatically selected from the top of the list every time a new cassette is inserted.

What is claimed is:

1. A radiation image reading apparatus, comprising:
   a memory to memorize information regarding each of a plurality of subjects as reservation data for each subject;
   a plurality of slots into each of which a recording medium recording a radiation image can be loaded;
   selecting means for selecting at least one reservation data for a subject from said plural reservation data;
   correlating means for correlating said selected reservation data with at least one of said plurality of slots;
   registration list preparing means for preparing a registration list based on said selected reservation data; and
   a display to display said registration list.

2. The radiation image reading apparatus of claim 1, further comprising:
   a detector to detect a slot into which said recording medium is loaded, among said plurality of slots.

3. The radiation image reading apparatus of claim 1, wherein said display is capable of displaying said reservation data in a reservation list, and said correlating means correlates a specific reservation data, which is designated out of said reservation data displayed on said reservation list by said display, with an identification of said slot.

4. The radiation image reading apparatus of claim 3, wherein said correlating means correlates a loading order, by which said recording mediums are loaded into said plurality of slots, with said reservation data.

5. The radiation image reading apparatus of claim 3, further comprising:

warning means for warning when a reading registration is not processed within a predetermined period of time, after said recording medium is loaded into said slot.

6. The radiation image reading apparatus of claim 5, wherein said display displays a warning message based on warning by said warning means.

7. The radiation image reading apparatus of claim 3, further comprising:

warning means for warning, when said reading registration is not processed within a predetermined period of time, after said reservation data is selected.

8. The radiation image reading apparatus of claim 3, wherein an reservation selection is performed from a top of said reservation list, when said recording medium is loaded into a slot.

9. The radiation image reading apparatus of claim 1, further comprising:

reading means for reading said radiation image recorded, on said recording medium, wherein said display is capable of displaying processing status of said reading means.

10. The radiation image reading apparatus of claim 9, wherein said display is capable of displaying reading order of plurality of said recording mediums.

11. A radiation image reading apparatus, comprising:

a plurality of slots into each of which a recording medium recording a radiation image can be loaded;

reserving means for reserving relevant data which corresponds to a radiation image to be read and for memorizing said plurality of relevant data;

registering means for registering a reserved relevant data for a reading operation among said plurality of relevant data; and a display to display said registered relevant data.

12. The radiation image reading apparatus of claim 11, further comprising:

warning means for showing a warning message when either an image outputting mode or a re-exposure mode is not selected within a predetermined period of time.

13. The radiation image reading apparatus of claim 11, wherein said registering means registers a reserved relevant data on a screen, a radiation image corresponding to said registered relevant data is read by a reading means and said read radiation image and said registration list are displayed on the same screen on which said reserved relevant data is registered.

14. The radiation image reading apparatus of claim 11, wherein said recording medium, being loaded into said slots in accordance with a loading order, is correlated with one of said plurality of relevant data, being selected in accordance with a selected order, by correlating said loading order with said selected order.

15. The radiation image reading apparatus of claim 14, further comprising:

warning means for warning when a reading registration is not processed within a predetermined period of time, after said cassette is loaded into said slot.

16. The radiation image reading apparatus of claim 14, further comprising:

warning means for warning when said reading registration is not processed within a predetermined period of time, after said reservation data is selected.

17. The radiation image reading apparatus of claim 14, wherein an reservation selection is performed from a top of said reservation list, when said recording medium is loaded into a slot.

18. The radiation image reading apparatus of claim 14, wherein said loading order is a resultant loading order, when said plurality of recording mediums are arbitrarily loaded into said plurality of slots.

19. A radiation image reading apparatus, comprising:

a plurality of slots into each of which a recording medium recording a radiation image can be loaded;

reserving means for reserving relevant data which corresponds to a radiation image to be read and for memorizing said relevant data;

registering means for registering a reserved relevant data for a reading operation among said plurality of relevant data;

reading means for reading a radiation image of said registered relevant data and for outputting radiation image data; and a memory to memorize said radiation image data of said registered relevant data.

* * * * *